United States Patent [19]
Oreglia et al.

[11] Patent Number: 5,470,624
[45] Date of Patent: Nov. 28, 1995

[54] OSTOMY FILM

[75] Inventors: Aurelio Oreglia, Como; Paolo Vietto, Legnano, both of Italy

[73] Assignee: W. R. Grace & Co.-Conn., Duncan, S.C.

[21] Appl. No.: 419,786

[22] Filed: Apr. 11, 1995

Related U.S. Application Data

[62] Division of Ser. No. 363,565, Dec. 22, 1924, which is a continuation of Ser. No. 951,034, Sep. 24, 1992, abandoned, which is a continuation of Ser. No. 626,368, Dec. 12, 1990, abandoned.

[30] Foreign Application Priority Data

Dec. 13, 1989 [GB] United Kingdom ............ 8928221

[51] Int. Cl.$^6$ .................... B29D 23/00; B32B 27/36; D04H 1/58
[52] U.S. Cl. .................. 428/36.1; 428/36.2; 428/36.6; 428/35.9; 428/286; 428/287; 428/290; 428/296; 428/36.7; 428/216; 428/340; 428/518; 428/520
[58] Field of Search .................. 428/36.1, 36.2, 428/36.6, 246, 286, 287, 288, 290, 296, 340, 518, 520

[56] References Cited

U.S. PATENT DOCUMENTS

| | | | |
|---|---|---|---|
| 4,284,671 | 8/1981 | Cancico et al. | 428/35 |
| 4,525,396 | 6/1985 | Takasa et al. | 428/35 |
| 4,606,970 | 8/1986 | Sharps | 428/301 |
| 4,687,692 | 8/1987 | Akao | 428/137 |
| 4,975,316 | 12/1990 | Romanowski | 428/247 |
| 5,110,643 | 5/1992 | Akao et al. | 428/213 |

FOREIGN PATENT DOCUMENTS

| | | |
|---|---|---|
| 0611459 | 7/1988 | Australia . |
| 0600363 | 12/1988 | Australia . |
| 0621048 | 4/1989 | Australia . |
| 0167956 | 1/1986 | European Pat. Off. . |
| 0273611 | 7/1988 | European Pat. Off. . |
| 0318025 | 5/1989 | European Pat. Off. . |
| 60-206622 | 10/1985 | Japan . |
| 2023494 | 1/1980 | United Kingdom . |
| 2064333 | 6/1981 | United Kingdom . |
| 2115291 | 9/1983 | United Kingdom . |
| 2122134 | 1/1984 | United Kingdom . |
| 2138431 | 10/1984 | United Kingdom . |
| 2211196 | 6/1989 | United Kingdom . |
| 0164438 | 12/1989 | WIPO . |

Primary Examiner—George F. Lesmes
Assistant Examiner—Kathryne E. Shelborne
Attorney, Agent, or Firm—Thomas C. Lagaly; Mark B. Quatt; William D. Lee

[57] ABSTRACT

The invention provides a sheet material which comprises a non-woven plastics film and bonded thereto without an adhesive, a barrier film; the sheet material is especially useful for the production of ostomy bags.

15 Claims, No Drawings

OSTOMY FILM

This is a divisional of application Ser. No. 08/363,565, filed Dec. 22, 1994, which in turn is a continuation of application Ser. No. 07/951,034, filed on Sep. 24, 1992 and now abandoned, which in turn is a continuation of application Ser. No. 07/626,368, filed De. 12, 1990 and now abandoned.

This invention relates to a new film material which is particularly suitable for ostomy bags.

More particularly the invention provides novel laminated film structures which combine exceptional softness, low noise generation, comfort in wear, light weight and mechanical strength which render them particularly suitable for the manufacture of containers and bags, such as ostomy pouches, intended for human drainage in medical applications particularly for the collection of excretion products from patients who have undergone surgical reconstruction of their excretive system.

The primary requirements for materials for the construction of ostomy bags are softness, barrier to odour, light weight and a comfortable feel to the skin. These requirements are usually met in existing laminates by combining a barrier film, which may be a monolayer or multilayer construction, and which is typically in the range of 60 to 100 micrometres thick, with a skin contact substrate material, either non woven or perforated which is secured to the barrier film through a peripheral pouch seal.

Such a construction, however, possesses two main drawbacks. It is very bulky and during normal use can become waterlogged, for example after a shower, by the entrapment of water between the backing layer and the film.

The problem of entrappeal water might be met by the use of an adhesive between the two layers but this would render the pouch even more bulky and much stiffer. The use of a thinner film, without adhesive, would solve the problem of bulk but would not solve the problem of water entrapment and, more importantly, would deprive the laminate of its strength, leaving it unacceptably weak.

An additional problem with ostomy bags is the noise which they generate as the wearer moves thereby revealing their presence. Ostomy bag users may wish their use of such bags not to be revealed v. It is therefore desirable that the bags should not generate noise, for example by rustling, as a wearer moves.

It has now been discovered that a thin barrier film can be laminated with a thin non-woven film by heat lamination, optionally in conjunction with corona bonding, without the use of adhesive, to produce an intimate bond between the two films. The resulting film structure possesses exceptional softness, lightness, low noise generation and mechanical strength which renders it especially suitable for use in the construction of ostomy pouches.

The present invention accordingly provides a sheet material which comprises a non-woven plastics film and, bonded thereto without an adhesive, a barrier film.

The term "adhesive" as used in to is specification including the accompanying claims means a conventional solvent adhesive which would generally lead to quite a stiff sheet material.

The total thickness of the sheet material is generally 50 to 200, preferably 75 to 100 micrometers. The thickness of the barrier layer will generally not be more than 20 to 25 micrometers. The total thickness of the barrier film is preferably less than about 40 and is most preferably 20 to 40) micrometers. The thickness of the barrier layer itself is preferably 5 to 15 most preferably about 10) micrometers. Lower thicknesses may also be used, for example 3 to 10 most preferably about 5) micrometers. Such lower thicknesses are preferred when the barrier material is, for example an ethylene-vinyl alcohol copolymer.

Suitable non-woven films comprise, for example, spun bonded polyester, EVA (.ethylene vinyl acetate), polypropylene, VLDPE (very low density polyethylene) or, preferably, LDPE low density polyethylene), most preferably LLDPE (linear low density polyethylene).

Non-woven films having a weight of 15 to 40 $gm^2$ are preferred; films of about 25 $gm^2$ are most preferred.

The barrier film may comprise one or, preferably more layers. Conventional gas and odour barrier materials may be used, such as vinylidene chloride copolymers with a comonomer, for example an acrylic ester, acrylic acid, and vinyl chloride, or an ethylene-vinyl alcohol copolymer, or vinylidene fluoride-vinyl fluoride copolymer, or polyamides, or mixtures thereof, with the optional addition of chlorinated paraffins, stabilisers and waxes. A coextruded film comprising PVDC (polyvinylidene chloride) and preferably also comprising an EVA layer is preferred. PVDC/EVA films, particularly EVA/PVDC/EVA, are preferred. Similar films comprising an ethylene vinyl alcohol copolymer and preferably also comprising an EVA layer are also of interest, preferably an EVA/Tie/EVOH/Tie/EVA barrier material. The tie layer is preferably a modified EVA as described hereinafter.

In order to produce an intimate bond between the non-woven and barrier films they should comprise polymers which have a high affinity for each other and are able to develop at a relatively low temperature, preferably less than 80° C., a permanent bond which is necessary to ensure the integrity of pouches constructed from the layers. It will be understood that the strength of the bond will depend upon the temperature, pressure and time used in the bonding process.

Heat lamination of the non-woven and barrier films is preferably carried out using an oven temperature of 70°–120° C., preferably about 80° C., applied to the non-woven layer. A calendar temperature of 60°–100° C., preferably about 80° C., applied to the non-woven layer is preferred. The temperature of the nip rolls is preferably 50–°80° C., particularly about 60° C. (applied to the whole material). When corona bonding is used in conjunction with heat lamination, as is preferred, 3–6 k pm a 1 m width is preferably used, depending on the line speed. It will be understood that the temperatures used will also depend upon line speed. By way of example the Examples hereinafter illustrate preferred conditions for a line speed of 15 m/min: higher temperatures and speeds may be used in industrial production.

The layer of barrier film in contact with the non-woven film should have a high affinity for the material of the non-woven film. When the non-woven film is a polyethylene, EVA is particularly preferred as the "contact" layer in the barrier film. The EVA contact layer preferably comprises about 26% to 28% of vinyl acetate. When the barrier film has the structure EVA/barrier/EVA the EVA layer on the opposite side to the EVA layer in contact with the non-woven material preferably comprises a lower proportion of vinyl acetate, most preferably about 18%. Tie layers may also be introduced, in order to improve bonding, between the barrier layer and the EVA layer. Such tie layers may comprise modified EVA. Modified EVA, for example comprising grafted groups derived from an anhydride, e.g. maleic anhydride, is preferred. This will ensure easier bonding to the non-woven material at relatively low temperature and good seal strength at the seal between the two films. The "contact" layer, in addition to its action as a bonding agent can also help to avoid curling of the film and contribute to the mechanical strength of the sheet material and containers made from it.

Other suitable materials include ionomers, preferably those having a low VICAT point, e.g. Surlyn 1702, free acid ionomers, e.g. NUCREL by Du Pont, EBA's, EMA's, high melt index PE's and chlorinated PE: not all of these would bond to PVDC, requiring a tie layer in between.

In the barrier film used in the invention a sealing layer is generally provided on the side of the barrier layer remote from the non-woven material. This layer may be an EVA as hereinbefore described, for heat sealing. Other materials can be used in place of EVA, for example EBA, ionomer, LDPE, chlorinated polyethylene, LLDPE and VLDPE with densities of 0.860 to 0.925 g/cc, EMA and EAA (as also indicated as bonding to the non-woven).

The polyvinylidene chloride used as a barrier layer may comprise vinyl chloride to provide a softer material although PVDC comprising methyl acrylate may also be used. When vinyl chloride is the comonomer a mixture of emulsion and suspension polymerised material, for example in a ratio of 9 (emulsion polymerisad) : 1 (suspension polymerised) PVDC is particularly preferred.

It is also preferred to reduce the quantity of plasticizer which would normally be present in the PVDC. Increased amounts of plasticizer generally lead to a film having inferior barrier properties. PVDC films comprising less plasticizer may have a lower thermal stability and small quantities of a mineral thermal stabilizer (for example hydroxytacte or sodium pyrophosphate)-may be used to alleviate this problem.

The term "LLDPE" or "linear lower density polyethylene" are used herein to describe copolymers of ethylene with one or more comonomers preferably selected from $C_4$–$C_{10}$ olefins such as butylene and octene in which the molecules of the copolymers comprise long chains with few side chain branches or cross-link structures. This molecular structure is to be contrasted with conventional low density polyethylenes which are more highly branched than their linear low density counterparts. LLDPE may also be characterised by the low pressure, low temperature processes used to produce it. LLDPE as defined herein has a density which is usually in the range of about 0.916 g/cc to about 0.925 g/cc.

The term "VLDPE" or "very low density polyethylene" as used herein refers to linear polyethylene copolymers having a density usually in the range of less than about 0.912 g/cc to about 0.860 g/cc.

The term "EVA" or "ethylene vinyl acetate copolymer" as used herein refer to a copolymer formed with ethylene and vinyl acetate monomers in which the ethylene derived units in the copolymer are present in major amounts, preferably from about 60 to 98% by weight, and the vinyl acetate-derived units in the copolymer are present in minor amounts, preferably from about 2 to 40 percent by weight of the total. The EVA film preferably has a high vinyl acetate content, for example 18 to 28%: about 28% is especially preferred.

The term "ionomer" as used herein is, for example, a copolymer of ethylene and a vinyl monomer with an acid group, usually an ethylenically unsaturated carboxylic acid which is generally mono-basic, for example acrylic or methacrylic acid. It is to be understood that the term "ionomer" as used in this specification includes both the free acid and ionised form. The ionised form is preferable to the free acid form. The neutralising cation may be any suitable metal ion, for example an alkali metal ion, such as sodium, a zinc ion or other multivalent metal ion. Suitable ionomers include those sold under the trademark Surlyn, e.g. Surlyn A and Surlyn B, marketed by Du Pont.

The term "polyvinylidene chloride" as used herein includes vinylidene chloride copolymers such as those sold under the brand name "Saran" by Dow Chemical Company of the United States and which usually comprise at least 50% vinylidene chloride monomer with, as the comonomer, vinyl chloride or methyl acrylate, or another suitable comonomer.

Preferred EVOH materials are, for example EVAL,* EP F 301B (Kuraray) or Selar* OH 4416 (Du Pont). Other EVOH materials of high (e.g. 44%) ethylene content are also preferred, thereby providing flexibility and softness at the thicknesses used.

It is to be understood that percentages in this specification, including the accompanying claims, are calculated on a "by weight" basis unless otherwise specified.

The invention also provides a container formed from a film according to the invention and in particular such a container in the form of an ostomy pouch. Ostomy pouches can be formed with the non-woven layer on the outside to provide a construction which is comfortable in contact with the skin, light in weight and strong. The non-woven layer can provide water repellancy and this, in combination with the intimate bond with the barrier layer, reduces or prevents waterlogging of the pouch when, for example, the wearer takes a shower.

The following Examples illustrate the invention.

EXAMPLE 1

A film material according to the invention may be produced by heat laminating the following:

Non-woven layer: 25 or 40 g/m² spun bonded linear (preferably ASPUN** (Dow));

Barrier film: EVA/PVDC/EVA* 5/10/20 micrometers or 10/10/20 micrometers.

Heat lamination provides a film having the following structure:

EVA/PVDC/EVA* non-woven layer.

*The laminating contact layer of EVA comprises 28% by weight of vinyl acetate.

*ASPUN is LLDPE-based.

Corona bonding may be used in conjunction with heat lamination.

Suitable conditions for the lamination process are as follows:

Speed: 15 m/min

Oven Temperature: 80° C. (applied to the non woven layer)

Calendar Temperature: 80° C. (applied to the non woven layer)

Nip rolls temperature : 60° C. (applied to the whole material) .

Corona discharge: 3 kw on 1 m width to obtain 52 dyne/cm.

Higher temperatures and speeds may be used in industrial production.

EXAMPLE 2

A film material according to the invention may be produced by heat laminating the following:

Non-woven layer: 25 or 40 g/m² spun bonded linear PE (preferably ASPUN (Dow));

Barrier film :EVA/Tie$^1$/EVOH$^3$/Tie$^1$/EVA$^2$

Heat lamination provides a film having the following structure:

EVA/Tie$^1$/EVOH3/Tie$^1$/EVA$^2$/non-woven layer, $^1$ Modified EVA, comprising grafted anhydride, preferably maleic anhydride.

$^2$ The laminating contact layer of EVA comprises 28% by weight of vinyl acetate.

$^3$ EVAL* EP F 301B (Kuraray) or Selar* OH 4416 (Du Pont): other EVOH polymers of high ethylene content (44%) may be used, thereby providing sufficient flexibility and softness at a thickness of 3–10, preferably about 5 micrometers.

Suitable conditions for the heat lamination and corona bonding are as described in Example 1. As in Example 1 higher temperatures and speeds may be used in industrial production.

It is to be understood that the term "non-woven film" as used in this specification including the accompanying claims means, for example, a non-woven web, material or fabric.

We claim:

1. A container formed from a sheet material which comprises a nonwoven plastics film and, bonded thereto without an adhesive, a gas and odor barrier film, said barrier film comprising, in the following order:

a contact layer in contact with said non-woven film and having a high affinity for the material of said non-woven film;

a gas barrier layer; and a sealing layer.

2. The container of claim 1, wherein said contact layer is formed from a material selected from the group consisting of ethylene-vinyl acetate copolymer, ionomer, ethylene-butyl acrylate copolymer, ethylenemethyl acrylate copolymer, high melt index polyethylene, and chlorinated polyethylene.

3. The container of claim 2, wherein said contact layer comprises ethylene-vinyl acetate copolymer.

4. The container of claim 1, wherein said barrier layer is formed from a material selected from the group consisting of polyvinylidene chloride; vinylidene chloride copolymer with an acrylic ester, acrylic acid, or vinyl chloride copolymer; ethylene-vinyl alcohol copolymer; vinylidene fluoride-vinyl fluoride copolymer; polyamides; and mixtures of the foregoing.

5. The container of claim 5, wherein said sealing layer is formed from a material selected from the group consisting of ethylene-vinyl acetate copolymer, ethylene-butyl acrylate copolymer, ionomer, low density polyethylene, chlorinated polyethylene, linear low density polyethylene, very low density polyethylene, ethylene-methyl acrylate copolymer, and ethylene-acrylic acid copolymer.

6. The container of claim 5 wherein said sealing layer comprises ethylene-vinyl acetate copolymer.

7. The container of claim 1, further including:

a tie layer positioned between said barrier layer and said contact layer; and a tie layer positioned between said barrier layer and said sealing layer.

8. The container of claim 7, wherein said tie layers comprise ethylene vinyl acetate copolymer modified with maleic anhydride.

9. The container of claim 1, wherein:

said non-woven film comprises linear low density polyethylene;

said contact layer comprises ethylene vinyl acetate copolymer;

said barrier layer comprises polyvinylidene chloride; and said sealing layer comprises ethylene vinyl acetate copolymer.

10. The container of claim 9, further including:

a tie layer positioned between said barrier layer and said contact layer; and a tie lie layer positioned between said barrier layer and said sealing layer.

11. The container of claim 10, wherein said tic layers comprise ethylene vinyl acetate copolymer modified with maleic anhydride.

12. The container of claim 1, wherein said sheet material has a thickness of 75 to 100 micrometers.

13. The container of claim 1, wherein said gas and odor barrier film has a thickness of 20 to 40 micrometers.

14. The container of claim 1, wherein said barrier layer has a thickness of 5 to 15 micrometers.

15. The container of claim 1, wherein said container is in the form of an ostomy pouch.

\* \* \* \* \*